(12) United States Patent
O'Meara

(10) Patent No.: US 8,504,387 B1
(45) Date of Patent: Aug. 6, 2013

(54) OPTIMIZED SPECIMEN COLLECTION FOR LABORATORY TESTS

(75) Inventor: Jason Lawrence O'Meara, Cary, NC (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 116 days.

(21) Appl. No.: 13/212,662

(22) Filed: Aug. 18, 2011

Related U.S. Application Data

(63) Continuation of application No. 12/981,841, filed on Dec. 30, 2010, now abandoned.

(60) Provisional application No. 61/291,746, filed on Dec. 31, 2009.

(51) Int. Cl.
*G06Q 10/00* (2012.01)
*G06Q 50/00* (2012.01)

(52) U.S. Cl.
USPC ........................................ 705/2; 705/3; 702/1

(58) Field of Classification Search
USPC ............................................ 705/2–3; 702/1
See application file for complete search history.

(56) References Cited

U.S. PATENT DOCUMENTS

| | | | | |
|---|---|---|---|---|
| 2001/0051880 | A1* | 12/2001 | Schurenberg et al. | 705/3 |
| 2005/0159982 | A1* | 7/2005 | Showalter et al. | 705/2 |
| 2008/0300789 | A1* | 12/2008 | Fritchie et al. | 702/1 |

OTHER PUBLICATIONS

Kiechle et al., Satellite Laboratories: A cost-benefit study, Nov. 1998, Medical Laboratory Observer, pp. 44-50.*

* cited by examiner

*Primary Examiner* — Luke Gilligan
(74) *Attorney, Agent, or Firm* — Jon E. Gordon; Frommer Lawrence & Haug LLP

(57) ABSTRACT

Embodiments of the invention relate to methods of optimizing the collection of specimens, e.g., of blood, when multiple laboratory tests have been prescribed at one time for a patient. Laboratory tests may use specimens such as blood drawn, e.g., through venipuncture, and patients may experience greater discomfort, inconvenience, and/or anxiety as more and more blood is collected, and at greater expense. Embodiments of the invention include computer systems configured to optimize the collection of specimens for laboratory tests to reduce the number of specimens that must be collected from a patient for any given set of laboratory tests.

15 Claims, 5 Drawing Sheets

OPTIMIZED SPECIMEN COLLECTION FOR LABORATORY TESTS

CROSS REFERENCE TO RELATED APPLICATION

This application is a continuation of U.S. application Ser. No. 12/981,841, filed Dec. 30, 2010 now abandoned; this application also claims the benefit of U.S. Provisional Application Ser. No. 61/291,746, filed Dec. 31, 2009, which is incorporated by reference herein in its entirety, including without limitation all appendices thereto.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent files or records but otherwise reserves all copyrights whatsoever.

BACKGROUND

Laboratory testing plays an important and growing role in health care delivery. With this increased role may come an increase in the number of tests to which a patient may be subjected, however. Considering that tests may use specimens such as blood drawn, e.g., through venipuncture, patients may experience greater discomfort, inconvenience, and/or anxiety as more and more blood is collected. If each separate test uses a distinct specimen that is collected in its own container, moreover, participants in the testing process may incur greater expense and inconvenience as they handle more containers.

BRIEF SUMMARY OF THE INVENTION

Embodiments of the invention relate to methods of optimizing the collection of specimens, e.g., of blood, when multiple tests have been prescribed at one time for a patient. Embodiments of the invention include computer systems configured to identify and/or provide optimized procedures for collecting one or more specimens from a patient and computer-readable storage media encoded with instructions that may cause one or more computer systems to carry out or take part in such methods, identification, or provision.

According to an embodiment of the invention, a method is provided of optimizing collection of biological samples for a plurality of laboratory tests to be performed on a patient using a computer system that comprises one or more processors, one or more interfaces operatively coupled to at least one of the processors, and one or more computer-readable storage media operatively coupled to at least one of the processors. The method comprises receiving through one of the interfaces a requisition for the laboratory tests, each of the tests being associated with respective collection requirements including a required number of containers. The method further comprises, for each of the requisitioned tests, retrieving the associated collection requirements from the computer-readable storage medium. The method further comprises computing the total number of containers to be collected and determining that the number exceeds a collection limit. The method further comprises applying one or more optimizations until the collection cannot be further optimized or the optimized number of containers no longer exceeds the collection limit.

In an embodiment of the invention, optimization may proceed iteratively, with each iteration comprising replacing one container primarily associated with a first test with one aliquot from a container primarily associated with a second test that is not the first test. In an embodiment of the invention, the iterations continue until no further replacements can be made.

In an embodiment of the invention, selection of one or more rules or algorithms for optimization may depend on the total number of containers to be collected, the total collection limit or both.

Embodiments of the invention may be configured to optimize the collection of specimens, including collection limits, on the basis of specimen type. For example, collection of blood samples may be optimized or limited in a different manner than collection of urine samples, which may have different collection limits or other properties.

According to an embodiment of the invention, the computer systems configured to identify and/or provide optimized procedures for collecting one or more specimens from a patient may receive as input data from the point of collection, such as patient information. For example, a phlebotomist may input data collected while performing venipuncture, such as a patient's age or health disposition, to be used in providing o improving optimization.

Embodiments of the invention comprise computer systems programmed and/or otherwise configured to carry out these methods and computer-readable storage media encoded with instructions that, when executed by one or more processors within a computer system, cause the computer system to carry out these methods.

DETAILED DESCRIPTION OF PREFERRED EMBODIMENTS

Figure 1:
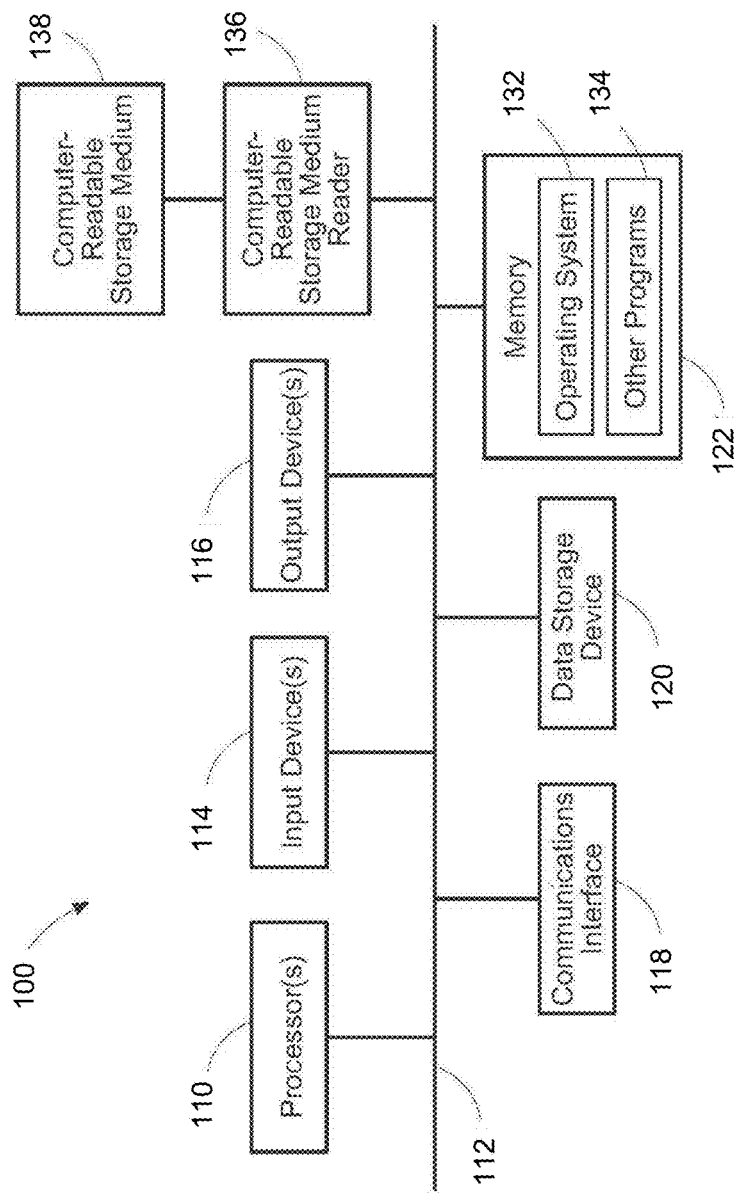
FIG. 1 is a block diagram depicting an exemplary computer system with which embodiments of the invention may at least partially be implemented.

Embodiments of the invention may be implemented by systems using one or more programmable digital computers. FIG. 1 depicts an example of one such computer system 100, which includes at least one processor 110, such as, e.g., an Intel or Advanced Micro Devices microprocessor, coupled to a communications channel or bus 112. The computer system 100 further includes at least one input device 114 such as, e.g., a keyboard, mouse, touch pad or screen, or other selection or pointing device, at least one output device 116 such as, e.g., an electronic display device, at least one communications interface 118, at least one data storage device 120 such as a magnetic disk or an optical disk, and memory 122 such as ROM and RAM, each coupled to the communications channel 112. The communications interface 118 may be coupled to a network (not depicted) such as the Internet.

Although the computer system 100 is shown in FIG. 1 to have only a single communications channel 112, a person skilled in the relevant arts will recognize that a computer system may have multiple channels (not depicted), including for example one or more busses, and that such channels may be interconnected, e.g., by one or more bridges. In such a configuration, components depicted in FIG. 1 as connected by a single channel 112 may interoperate, and may thereby be considered to be coupled to one another, despite being directly connected to different communications channels.

One skilled in the art will recognize that, although the data storage device 120 and memory 122 are depicted as different units, the data storage device 120 and memory 122 can be parts of the same unit or units, and that the functions of one can be shared in whole or in part by the other, e.g., as RAM disks, virtual memory, etc. It will also be appreciated that any particular computer may have multiple components of a given type, e.g., processors 110, input devices 114, communications interfaces 118, etc.

The data storage device 120 (FIG. 1) and/or memory 122 may store instructions executable by one or more processors or kinds of processors 110, data, or both. Some groups of instructions, possibly grouped with data, may make up one or more programs, which may include an operating system 132 such as Microsoft Windows®, Linux®, Mac OS®, or Unix®. Other programs 134 may be stored instead of or in addition to the operating system. It will be appreciated that a computer system may also be implemented on platforms and operating systems other than those mentioned. Any operating system 132 or other program 134, or any part of either, may be written using one or more programming languages such as, e.g., Java®, C, C++, C#, Visual Basic®, VB.NET®, Perl, Ruby, Python, or other programming languages, possibly using object oriented design and/or coding techniques.

One skilled in the art will recognize that the computer system 100 (FIG. 1) may also include additional components and/or systems, such as network connections, additional memory, additional processors, network interfaces, input/output busses, for example. One skilled in the art will also recognize that the programs and data may be received by and stored in the system in alternative ways. For example, a computer-readable storage medium (CRSM) reader 136, such as, e.g., a magnetic disk drive, magneto-optical drive, optical disk drive, or flash drive, may be coupled to the communications channel 112 for reading from a CRSM 138 such as, e.g., a magnetic disk, a magneto-optical disk, an optical disk, or flash RAM. Alternatively, one or more CRSM readers may be coupled to the rest of the computer system 100, e.g., through a network interface (not depicted) or a communications interface 118. In any such configuration, however, the computer system 100 may receive programs and/or data via the CRSM reader 136. Further, it will be appreciated that the term "memory" herein is intended to include various types of suitable data storage media, whether permanent or temporary, including among other things the data storage device 120, the memory 122, and the CSRM 138.

Figure 2:
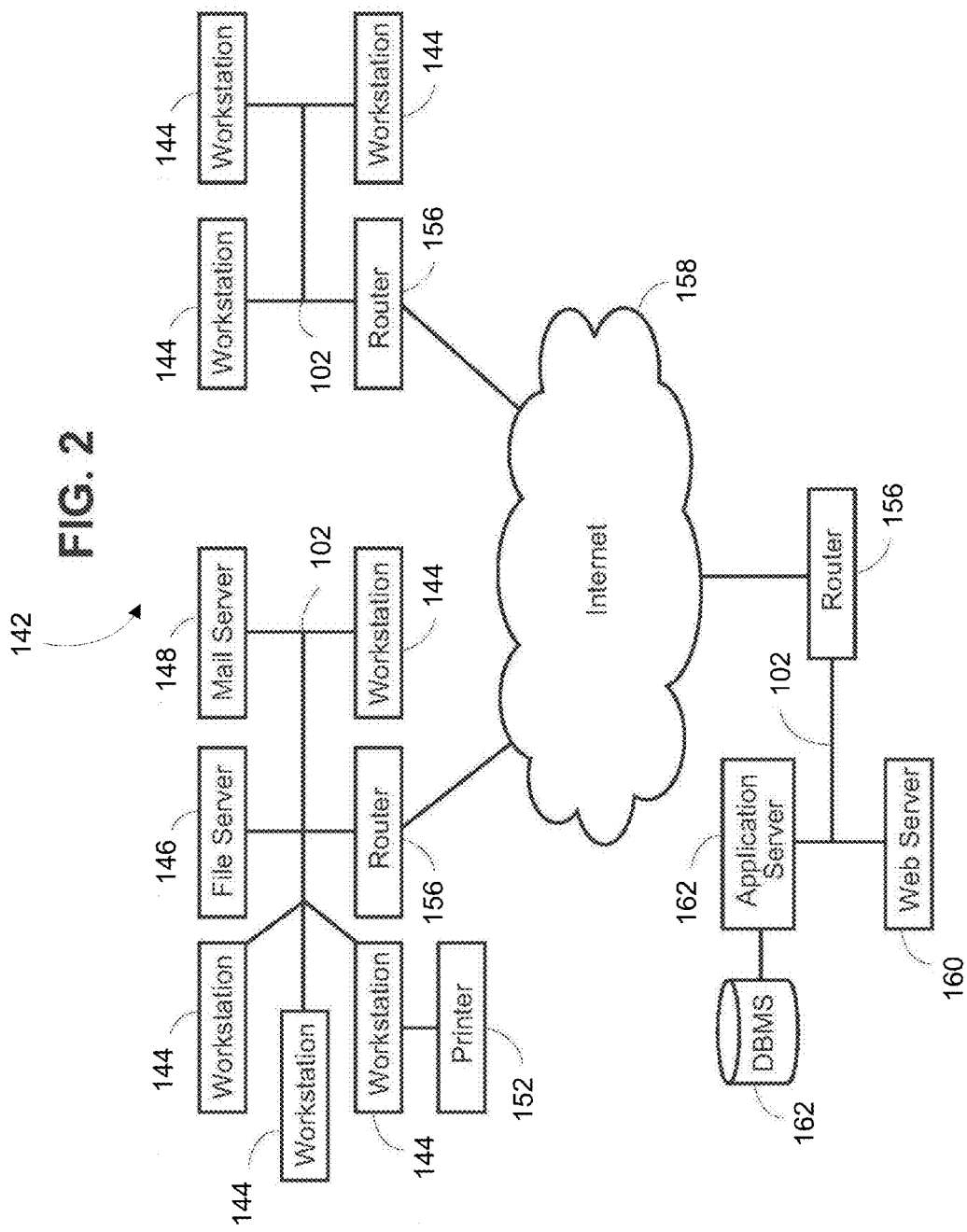
FIG. 2 is a block diagram depicting an exemplary interconnected network with which embodiments of the invention may at least partially be implemented.

Two or more computer systems 100 (FIG. 1) may communicate, e.g., in one or more networks, via, e.g., their respective communications interfaces 118 and/or network interfaces (not depicted). FIG. 2 is a block diagram depicting an example of one such interconnected network 142. Network 142 may, for example, connect one or more workstations 144 with each other and with other computer systems, such as file servers 146 or mail servers 148. A workstation 144 may comprise a computer system 100. The connection may be achieved tangibly, e.g., via Ethernet® or optical cables, or wirelessly, e.g., through use of modulated microwave signals according to the IEEE 802.11 family of standards. A computer workstation 144 or system 100 that participates in the network may send data to another computer workstation system in the network via the network connection.

One use of a network 142 (FIG. 2) is to enable a computer system to provide services to other computer systems, consume services provided by other computer systems, or both. For example, a file server 146 may provide common storage of files for one or more of the workstations 144 on a network 142. A workstation 144 sends data including a request for a file to the file server 146 via the network 142 and the file server 146 may respond by sending the data from the file back to the requesting workstation 144.

Further, a computer system may simultaneously act as a workstation, a server, and/or a client. For example, as depicted in FIG. 2, a workstation 144 is connected to a printer 152. That workstation 144 may allow users of other workstations on the network 142 to use the printer 152, thereby acting as a print server. At the same time, however, a user may be working at the workstation 144 on a document that is stored on the file server 146.

The network 142 (FIG. 2) may be connected to one or more other networks, e.g., via a router 156. A router 156 may also act as a firewall, monitoring and/or restricting the flow of data to and/or from the network 142 as configured to protect the network. A firewall may alternatively be a separate device (not pictured) from the router 156.

An internet may comprise a network of networks 142 (FIG. 2). The term "the Internet" refers to the worldwide network of interconnected, packet-switched data networks that uses the Internet Protocol (IP) to route and transfer data. In the example depicted in FIG. 3, the Internet 158 provides a communications network over which computer systems in network 142 communicate. For example, a client and server on different networks may communicate via the Internet 158, e.g., a workstation 144 may request a World Wide Web document from a Web Server 160. The Web Server 160 may process the request and pass it to, e.g., an Application Server 162. The Application Server 162 may then conduct further processing, which may include, for example, sending data to and/or receiving data from one or more other data sources. Such a data source may include, e.g., other servers on the same computer system 100 or LAN 102, or a different computer system or LAN and/or a Database Management System ("DBMS") 162.

As will be recognized by those skilled in the relevant art, the terms "workstation," "client," and "server" are used herein to describe a computer's function in a particular context. A workstation may, for example, be a computer that one or more users work with directly, e.g., through a keyboard and monitor directly coupled to the computer system. A computer system that requests a service through a network is often referred to as a client, and a computer system that provides a service is often referred to as a server. But any particular workstation may be indistinguishable in its hardware, configuration, operating system, and/or other software from a client, server, or both.

The terms "client" and "server" may describe programs and running processes instead of or in addition to their application to computer systems described above. Generally, a (software) client may consume information and/or computational services provided by a (software) server.

Embodiments of the invention relate to laboratory tests, e.g., for medical diagnosis, monitoring, or both. A laboratory test may involve one or more assays performed upon one or more samples of tissue and/or fluids obtained from a patient. For example, blood may be obtained from a patient, e.g., in a collection tube. The blood may be mixed with a coagulant, e.g., to separate the plasma, or an anticoagulant to keep the components mixed. As is well known in the art, the sample or a portion or aliquot of it may be, depending on the test, heated, chilled, spun in a centrifuge, mixed with one or more reagents, stained, subjected to spectroscopic analysis, and/or viewed through a microscope, to name only a few possibilities out of many.

Varied types of containers may be used to collect samples for laboratory testing. Commonly, blood samples may be collected into containers such as, e.g., the Vacutainer® or similar container, but other containers may be used. Containers may be made of suitable material, such as, e.g., glass or plastic, and a container may be designed to protect the contents, e.g., from light. A container may be manufactured or otherwise prepare so that it contains one or more substances (e.g., thrombin or sodium heparin, among many others), which may react with the sample in a way intended, e.g., to prepare and/or preserve the sample for transport and/or testing. (Depending on the context, otherwise identical containers that have been prepared in different ways may be considered different types of containers.)

For example, in connection with an embodiment of the invention, the containers listed in Table 1 may be available for use in collecting serum.

TABLE 1

Serum Collection Containers

| Container | Description | Estimated Serum Yield |
|---|---|---|
| SS | Serum Separator | 3.0 ml |
| S | Serum Transport Vial | 2.0 ml |
| XS | Non-Standard Serum Separator | 2.0 ml |
| V | Transport Vial | 2.0 ml |
| US | Un-Spun Serum Separator | 3.0 ml |
| RT | Red Top—No Gel | 4.0 ml |
| XX | Deferred Serum Separator | 3.0 ml |

Figure 3:
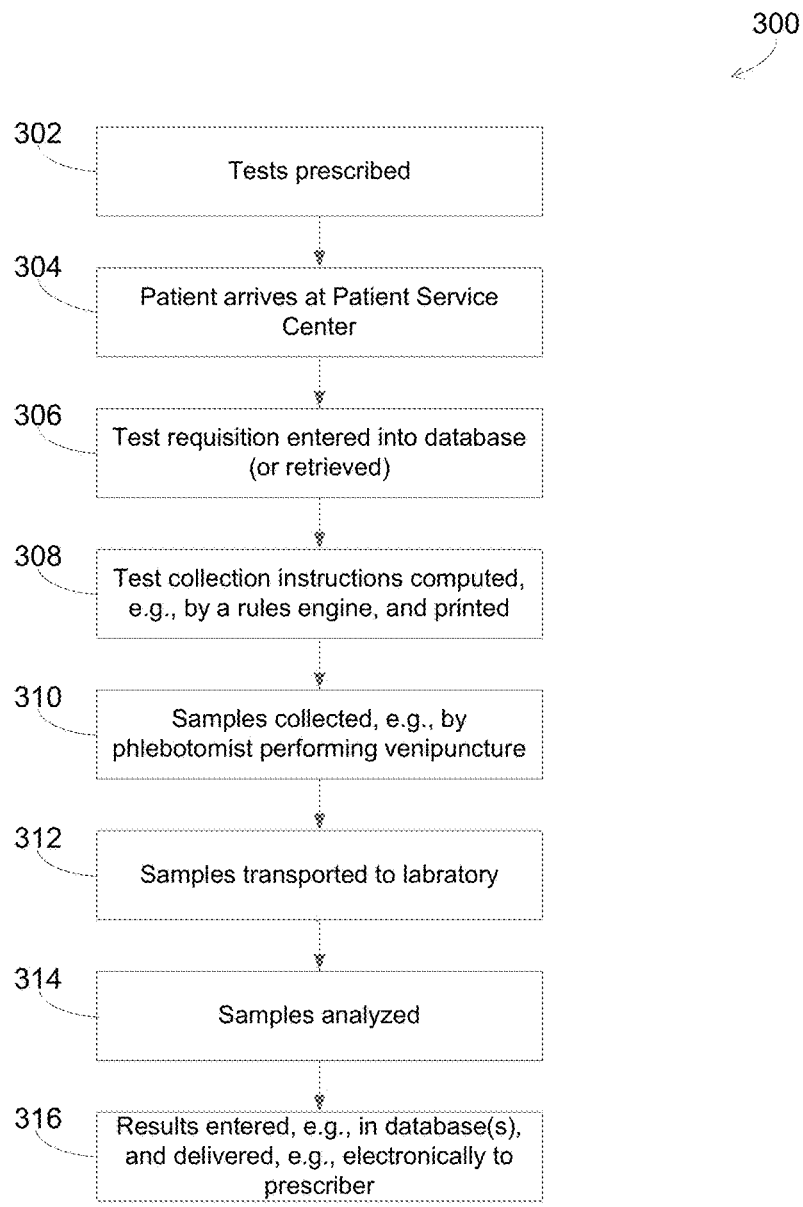
FIG. 3 depicts the flow of laboratory testing according to an embodiment of the invention.

FIG. 3 depicts the flow 300 of laboratory testing according to an embodiment of the invention. The process may begin, e.g., in block 302, when a physician or other health care provider prescribes or otherwise requests one or more tests for a patient. The request may take the form, for example, of a requisition form, signed by the physician, that provides information about the patient and the physician and specifies the requested test or tests. Alternatively, a requisition may be created electronically, and an electronic requisition may be transmitted electronically to a laboratory.

In block 304, the patient may go to a patient service center ("PSC") or other facility to have one or more samples collected for the test. If the patient carries a paper requisition, the information from the form may be entered, e.g., into an electronic database, in block 306. If a requisition was created electronically, the requisition may be retrieved, e.g., from a database, in block 306. The patient may provide other information, including, e.g., demographic, payment, and/or insurance information at the PSC as well.

In an embodiment, a patient, physician, or other service provider may enter information into, or retrieve information from, an electronic medical record, website, or other internet-enabled service or device, which may be electronically linked to the samples collected for purposes of optimization. Such information may be separate from, or combined with, any information derived from a traditional PSC setting.

In block 308, in an embodiment of the invention, instructions for collecting one or more samples from the patient may be computed, e.g., by a rules engine within a server or servers. The instructions in an embodiment of the invention may be provided to a technician or other person at the PSC, e.g., by displaying them on an electronic display device and/or by printing them.

In block 310, the samples are collected from the patient into containers, e.g., by a phlebotomist performing venipuncture or other means, depending, e.g., on the facility, test, and/or nature of the sample.

In block 312, the samples are taken to one or more laboratories for analysis in block 314. The results of the analysis may be recorded, e.g., in one or more electronic databases and/or be tangibly and/or electronically delivered to the prescriber in block 316.

It will be appreciated that a test may set requirements for the collection of the sample or samples. A test may specify, among other possibilities, that a certain volume, e.g., of blood, be collected, that it be collected in a particular container or type of container, and/or that the sample be handled in particular ways (e.g., that it be kept from light, or that it be refrigerated or frozen, among other requirements). The test requirements may allow for certain alternatives; for example, a test may specify that a particular container type is preferred, but that one or more alternatives would be acceptable.

For example, in an embodiment of the invention, collection requirements may be included in specimen handling logic (SHL) within an expert system. A collection of rows related to a single test may be referred to as an "SHL module." In an embodiment of the invention, each row of an SHL module has only a single specimen type, but one test may have rows with different specimen types. Table 2 lists the fields in a single row of an SHL module according to an embodiment of the invention.

TABLE 2

SHL Row Fields

| Field | Description |
|---|---|
| Order Code | Represents the test for which the order code is defined. |
| SP | The specimen type. |
| Q | May indicate the optimum specimen to perform the test, in terms of percentages (e.g., 100 may represent the maximum quality results if a test is to be performed on that specimen). In an embodiment of the invention, if more than one specimen is available for a work code, and all those specimens are valid for the test (i.e., they match more than one row of the SHL module), the row with the highest quality may be used first. |
| P | Lab preference of the specimen sample used. If more than one specimen is available with the same quality, the row with the highest preference (e.g., P = 1) may be used first. |
| US | Use specification, which may specify which specimen will be used first in the event that several specimens have the same quality and preference on a test. If may also define a "multiple" SHL, which may represent cases in which a test requires two different specimens. US starts with one for each order code. Two or more rows with the same number specify a multiple SHL. If more than one specimen or group of specimens is available for a test with the same quality and preference, the specimen or group with the first usage (e.g., US = 1) may be used first. |
| L | Lower replication limit, which may specify the minimum number of specimens of the same kind needed for performing this test. The value zero may indicate that this specimen is optional. |
| H | Higher replication level, which may specify the desired number of specimens of the same kind to perform the test. |

When a requisition asks for multiple tests for a patient, the technician at the collection site may simply treat the tests as independent and consequently satisfy the collection requirements for each test independently. An alternative may be desired, however, when the requisition calls for a substantial number of tests. For example, the greater number of samples may take longer to collect, which may increase the patient's discomfort and anxiety.

Figure 4:
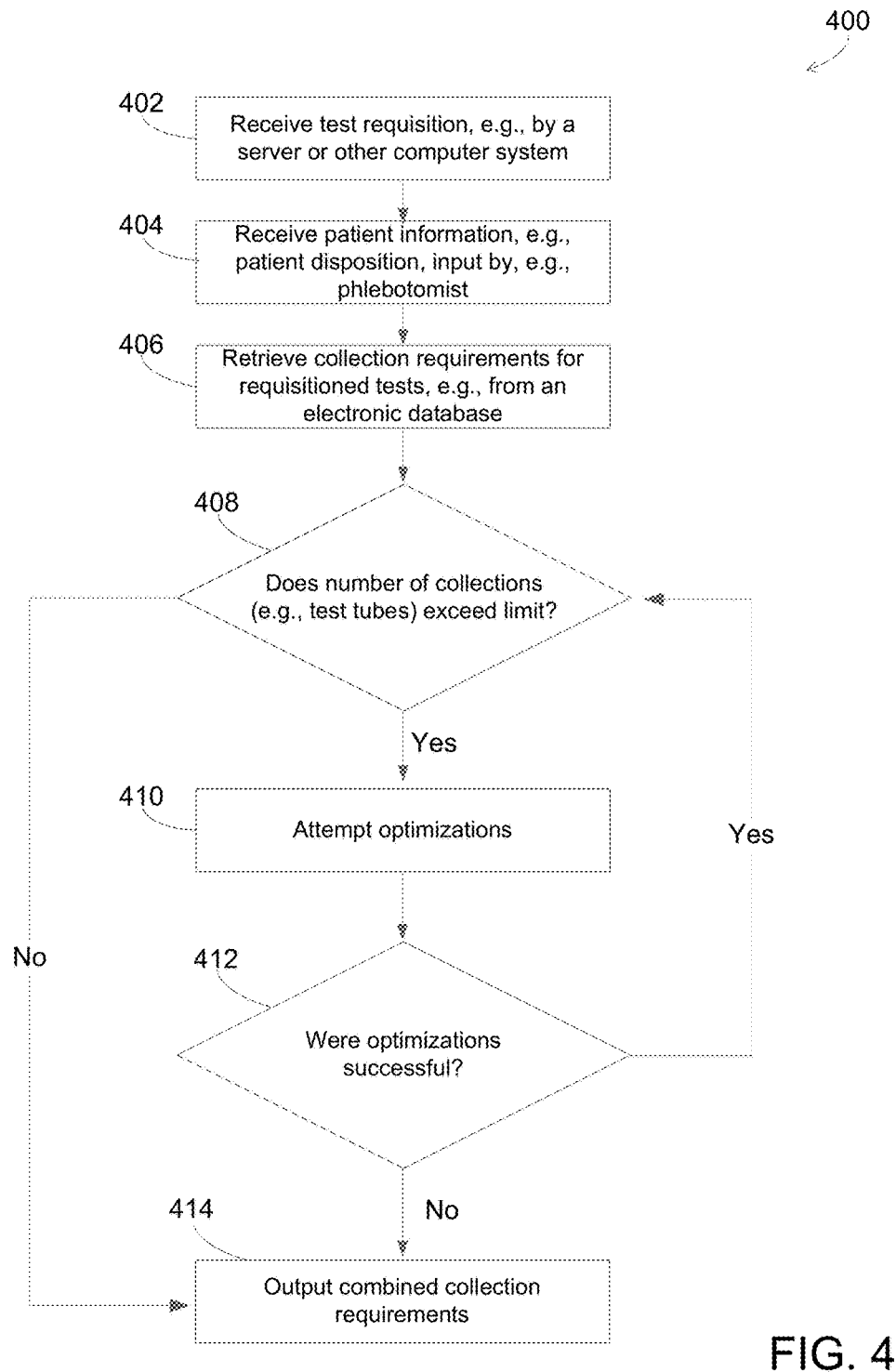
FIG. 4 depicts the flow of optimizing specimen collection according to an embodiment of the invention.

Thus, according to embodiments of the invention, systems and methods may attempt to optimize collection to reduce the number and/or volume of samples that may be collected when multiple tests are requisitioned for a patient at one time. FIG. 4 depicts the flow 400 of optimizing collection, e.g., by a computer system, according to an embodiment of the invention.

The depicted flow 400 begins in block 402 with receipt of the requisition, e.g., by a server or other computer system. The requisition may be transmitted electronically, e.g., from a physician as described above, or it may be entered manually, e.g., containing information from a printed requisition. The requisition may list one or more tests prescribed for the patient.

In block 404, patient information may be transmitted electronically, e.g., from a physician or patient service center, or it may be entered manually. The patient information received in block 404 may be used to vary the collection limit of block 408. For example, a phlebotomist may enter a patient's age or health disposition as an input to block 404. In such an example, the phlebotomist may assess that, for example, the patient's health disposition mandates less draw than the system's default limit, and the system should then optimize the draw for this requisition only to the downward-adjusted target for this patient, i.e., the collection limit of block 408 will be adjusted downward.

In block 406, the collection requirements for each of the requisitioned tests are retrieved, e.g., from an electronic database. These requirements may include the container types and amounts, collection volume, temperature and/or other handling instructions, etc. In an embodiment of the invention, the total number of containers (e.g., test tubes) may be computed and it may be determined in block 408 whether this total exceeds a total collection limit. If the number does not exceed this limit, collection instructions may be generated and output, e.g., electronically and/or in printed form, in block 414.

Figure 5:
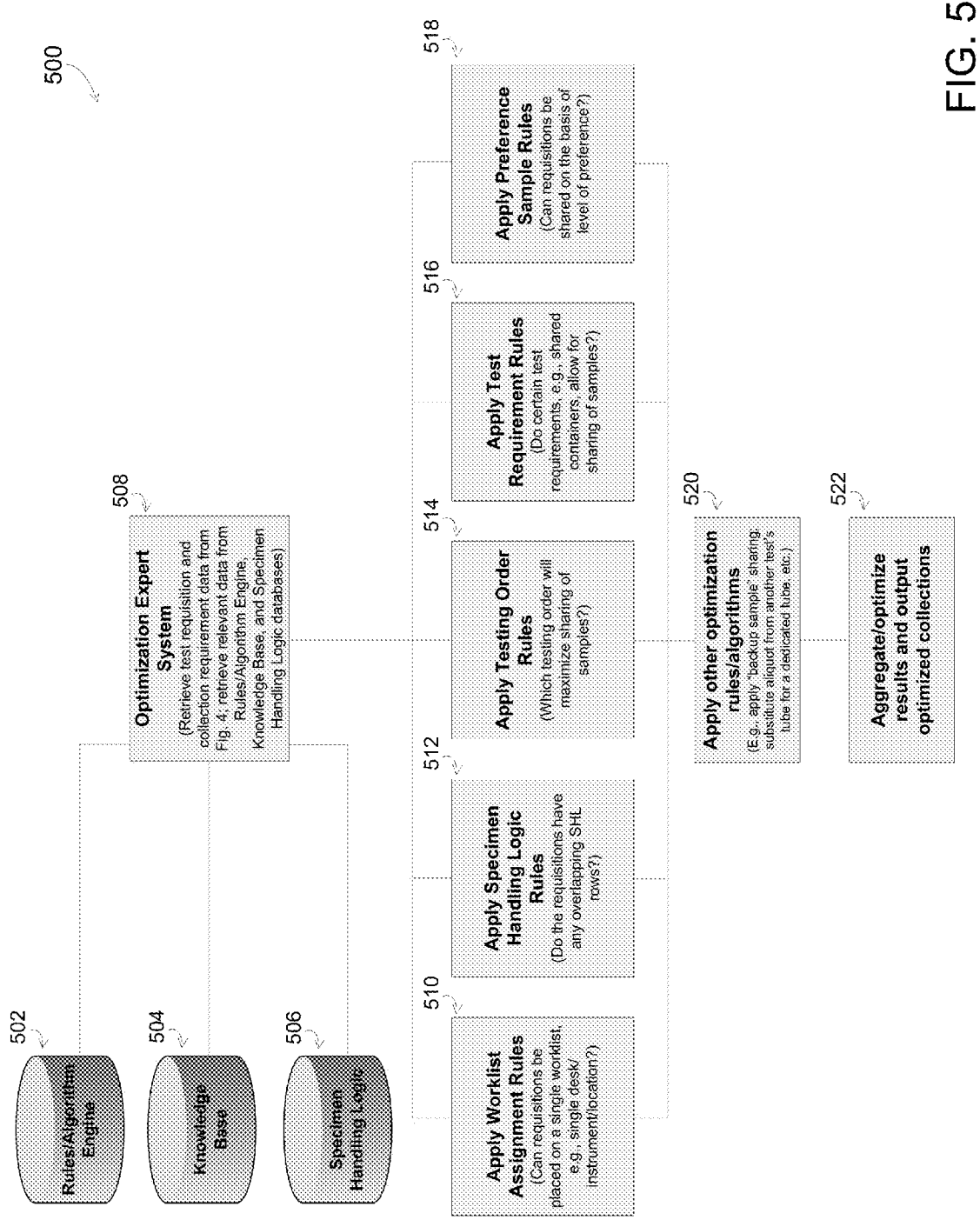
FIG. 5 depicts an exemplary set of optimizations according to an embodiment of the invention.

If the number does exceed the total collection limit, in an embodiment of the invention, various optimizations may be attempted in block 410 (and as further illustrated in exemplary FIG. 5). If it is determined in block 412 that no optimizations were possible, then, in an embodiment of the invention, collection instructions are generated and output in block 414.

If optimizations were made, however, in an embodiment of the invention, flow may return to block 408, where it may be determined whether the total number of collections still exceeds the total collection limit. If not, instructions may be generated and output in block 414. If so, further optimizations may be attempted by returning to block 410.

Many strategies, e.g., workflows, rules and/or algorithms, may be possible for optimizing collection in embodiments of the invention. Examples may generally entail substituting an aliquot from another test's tube for a dedicated tube for a test. In an embodiment of the invention, optimizations may be made, e.g., by an expert system, which may include a rules engine and a knowledge base comprising information about, e.g., the location and/or apparatus where test may be performed, compatibility between tests, collection requirements, analysis requirements, etc.

In an embodiment of the invention, optimization may proceed differently depending on the nature of the specimen and the process by which it is acquired. For example, venipuncture may be associated with discomfort, at least. Optimization of blood collection may therefore be more aggressive than that applied to collection of specimens less likely to hurt the donor, such as urine.

As example of a simple optimization is that which may take place when two requisitioned tests each specify identical containers and handling and the combined aliquot is smaller than the capacity of a single container. For example, a first test may require 0.2 ml from a serum separator (SS) tube at room temperature, while a second may also require 0.4 ml from such a tube, also at room temperature. In that case, in an embodiment of the invention, the requirements may be combined to specify 0.6 ml from a SS tube (which is less that the tube's estimated yield of 3.0 ml) at room temperature.

If the combined volume exceeds the capacity of the container, however, then two full containers of the shared type may be requested. For example, if the first test above required an aliquot of 2.5 ml, instead of 0.2 ml, and the second test required an aliquot of 1.0 ml, the result may be to specify collection of two full SS containers, each yielding 3.0 ml.

In an embodiment of the invention, specimens may never be optimized together if the temperatures are different. For example, in such an embodiment, a room temperature specimen may not be combined with one requiring refrigeration. Similarly, in an embodiment of the invention, specimens with different collection containers may not be optimized together.

Alternatively, in an embodiment of the invention, specimens with handling restrictions may be optimized together, with the most restrictive handling requirements being applied to the combined specimen. For example, if only one test requires a specimen to be protected from light, it may be combined with others that have no such requirement, so long as the shared container is protected from light.

Other optimization rules may reflect different SHL specified for different specimens. For example, tests specifying that a specimen aliquot from a shared tube may be optimized together, which tests requiring dedicated containers may not.

In an embodiment of the invention, optimization may be further limited to certain container, specimen, or handling types. For example, in one embodiment of the invention, optimization may be limited to SS or RT ("Red Top") containers.

It will be appreciated that the preceding examples are not limiting, however, and various other optimizations and/or limitations to optimization, instead of and/or in addition to some or all of the foregoing, will be apparent to persons skilled in the art.

FIG. 5 depicts an exemplary set of optimizations according to an embodiment of the invention, along with a rules/algorithm database/engine 502, a knowledge base database 504, and a specimen handling logic database 506.

With regard to optimization, for example, it may be determined that two or more tests on a requisition may be placed on the same worklist for a single desk, instrument, and/or location, as shown in block 510. In that case, in an embodiment of the invention, the tests may share a single sample.

In an embodiment of the invention, it may be determined that tests may share a sample, e.g., if their respective SHL modules include one or more common or overlapping rows, as shown in block 512.

It may further be determined that two tests may share a sample if the tests are performed in a particular order, as shown in block 514. For example, it may be determined that a CBC (complete blood count) may be performed on a sample that may subsequently be used for a blood lead analysis, but that a sample used for a blood lead analysis may not subsequently be used for a CBC. In an embodiment of the invention, an expert system may order the processing of a sample to maximize the opportunity for using each sample.

In an embodiment of the invention, an exhaustive search of the test requirements may be done to maximize sharing of samples that, e.g., may use the same container (including consideration of any preparation and/or handling of the container before and/or after collection), thereby minimizing the collection volume, as shown in block 516.

In connection with an embodiment of the invention, a sample may be considered the "preferred sample" for a test, e.g., if according to the appropriate SHL module, the container or specimen is configured with 100% quality, the first preference (P=1), and the first usage (US=1). In an embodiment of the invention, it may be determined that a test specifies a lower preference sample, e.g., as discussed above, but another test on the requisition also specifies this sample at some level of preference, and those tests may be designated to share this sample, as shown in block 518.

Additional optimization techniques, other than those shown in blocks 510 through 518, may be run as needed, for example, in block 520, or in any other suitable order. For example, as is known in the art, a test may specify collection of a larger amount than is used in a test, which may allow the test to be rerun without further collection if a first run is somehow spoiled. In an embodiment of the invention, these extra amounts may be reduced, e.g., by allowing multiple tests to share backups.

In an embodiment of the invention, as shown in block 522, a computer system may attempt more or less aggressively to merge samples or otherwise reduce the required collection depending, e.g., on the apparent number of containers or collection volume. For example, in an embodiment of the invention, the expert system may attempt only to share samples between tests on the same worklist if the original calculation shows that five containers would be needed, but may look for opportunities to use lower preference samples if the original calculation shows that eight or more containers would be needed.

While the invention has been described and illustrated in connection with embodiments, many variations and modifications as will be evident to those skilled in this art may be made without departing from the spirit and scope of the invention as defined by the claims, and the invention is thus not to be limited to the precise details of methodology or construction set forth above. For example, various optimization techniques may be used to reduce the number and/or volume of samples that may be collected when multiple tests are requisitioned, such as those described in the Appendix to U.S. Provisional Application Ser. No. 61/291,746, filed 31 Dec. 2009, and/or other optimization techniques not described herein. It is to be understood that such variations and modifications are intended to be included within the scope of the invention as defined by the claims.

The invention claimed is:

1. A computerized method of optimizing collection of biological samples for a plurality of laboratory tests to be performed on a patient, the method using a computer system that comprises one or more processors, one or more interfaces operatively coupled to at least one of the processors, and one or more computer-readable storage media operatively coupled to at least one of the processors, and the method comprising:

receiving through one of the interfaces a requisition for the laboratory tests, each of the tests being associated with respective collection requirements including a required number of containers;

for each of the requisitioned tests, retrieving the associated collection requirements from at least one of the computer-readable storage media;

at least one of the processors executing instructions to compute the total number of containers to be collected;

at least one of the processors executing instructions to determine that the number exceeds a collection limit; and at least one of the processors executing instructions to apply one or more optimizations until the collection cannot be further optimized or the optimized number of containers no longer exceeds the collection limit;

wherein optimization comprises at least one stage that comprises a plurality of iterations, each iteration comprising replacing one container primarily associated with a first test with one aliquot from a container primarily associated with a second test that is not the first test.

2. The computerized method of claim 1, wherein the iterations continue until no further replacements can be made.

3. The computerized method of claim 1, comprising automatic selection of one or more rules or algorithms for optimization, wherein selection of the one or more rules or algorithms for optimization depends on the total number of containers to be collected, the total collection limit, or both.

4. The computerized method of claim 1, wherein:

the laboratory tests comprise a first tests that require collection of blood samples and second tests that require collection of urine samples;

applying optimizations comprises applying at least one first optimization to blood collection and at least one second optimization to urine collection; and at least one first optimization is not one of the second optimizations.

5. The computerized method of claim 1, wherein at least one of the optimizations depends on one or more rules from a group that consists of:

a rule that depends on sharing of laboratory samples;

a rule that depends on assigning laboratory tests;

a rule that depends on specimen handing logic;

a rule that depends on determining the order of laboratory tests;

a rule that depends on the nature of an apparatus involved in the test;

a rule that depends on the location of an apparatus involved in the test;

a rule that depends on preference samples of laboratory tests;

a rule that depends on substituting aliquot from a first laboratory sample for a second laboratory sample; and a rule that depends on sharing of backup laboratory samples.

6. A computer system for optimizing the collection of specimens for laboratory tests, the computer system comprising:

one or more processors;

one or more interfaces operatively coupled to at least one of the processors; and one or more computer-readable storage media, operatively coupled to at least one of the processors and encoded with instructions that, when executed by one or more of the processors, cause the computer system at least to receive through one of the interfaces a requisition for the laboratory tests, each of the tests being associated with respective collection requirements including a required number of containers;

for each of the requisitioned tests, retrieve the associated collection requirements from at least one of the computer-readable storage media;

compute the total number of containers to be collected;

determine that the number exceeds a collection limit; and apply one or more optimizations until the collection cannot be further optimized or the optimized number of containers no longer exceeds the collection limit;

wherein optimization comprises at least one stage that comprises a plurality of iterations, each iteration comprising replacing one container primarily associated with a first test with one aliquot from a container primarily associated with a second test that is not the first test.

7. The computer system of claim 6, wherein the iterations continue until no further replacements can be made.

8. The computer system of claim 6, wherein:

the instructions comprise instructions that cause the computer system at least to select automatically one or more rules or algorithms for optimization; and selection of the one or more rules or algorithms for optimization depends on the total number of containers to be collected, the total collection limit, or both.

9. The computer system of claim 6, wherein:

the laboratory tests comprise a first tests that require collection of blood samples and second tests that require collection of urine samples;

applying optimizations comprises applying at least one first optimization to blood collection and at least one second optimization to urine collection; and at least one first optimization is not one of the second optimizations.

10. The computer system of claim 6, wherein at least one of the optimizations depends on one or more rules from a group that consists of:

a rule that depends on sharing of laboratory samples;

a rule that depends on assigning laboratory tests;

a rule that depends on specimen handing logic;

a rule that depends on determining the order of laboratory tests;

a rule that depends on the nature of an apparatus involved in the test;

a rule that depends on the location of an apparatus involved in the test;

a rule that depends on preference samples of laboratory tests;

a rule that depends on substituting aliquot from a first laboratory sample for a second laboratory sample; and a rule that depends on sharing of backup laboratory samples.

11. A non-transitory computer-readable storage medium encoded with instructions that, when executed by one or more processors comprised by a computer system that comprises one or more interfaces operatively coupled to at least one of the processors and one or more computer-readable storage media operatively coupled to at least one of the processors, cause the computer system to carry out a method of optimizing collection of biological samples for a plurality of laboratory tests to be performed on a patient, the method comprising:

receiving through one of the interfaces a requisition for the laboratory tests, each of the tests being associated with respective collection requirements including a required number of containers;

for each of the requisitioned tests, retrieving the associated collection requirements from at least one of the computer-readable storage media;

at least one of the processors executing instructions to compute the total number of containers to be collected;

at least one of the processors executing instructions to determine that the number exceeds a collection limit; and at least one of the processors executing instructions to apply one or more optimizations until the collection cannot be further optimized or the optimized number of containers no longer exceeds the collection limit wherein optimization comprises at least one stage that comprises a plurality of iterations, each iteration comprising replacing one container primarily associated with a first test with one aliquot from a container primarily associated with a second test that is not the first test.

12. The non-transitory computer-readable storage medium of claim 11, wherein the iterations continue until no further replacements can be made.

13. The non-transitory computer-readable storage medium of claim 11, wherein:

the instructions comprise instructions that cause the computer system at least to select automatically one or more rules or algorithms for optimization; and selection of the one or more rules or algorithms for optimization depends on the total number of containers to be collected, the total collection limit, or both.

14. The non-transitory computer-readable storage medium of claim 11, wherein:

the laboratory tests comprise a first tests that require collection of blood samples and second tests that require collection of urine samples;

applying optimizations comprises applying at least one first optimization to blood collection and at least one second optimization to urine collection; and at least one first optimization is not one of the second optimizations.

15. The non-transitory computer-readable storage medium of claim 11, wherein at least one of the optimizations depends on one or more rules from a group that consists of:

a rule that depends on sharing of laboratory samples;

a rule that depends on assigning laboratory tests;

a rule that depends on specimen handing logic;

a rule that depends on determining the order of laboratory tests;

a rule that depends on the nature of an apparatus involved in the test;

a rule that depends on the location of an apparatus involved in the test;

a rule that depends on preference samples of laboratory tests;

a rule that depends on substituting aliquot from a first laboratory sample for a second laboratory sample; and a rule that depends on sharing of backup laboratory samples.

* * * * *